US012616621B2

(12) United States Patent
Takahashi et al.

(10) Patent No.: US 12,616,621 B2
(45) Date of Patent: May 5, 2026

(54) ABSORBENT PRODUCT

(71) Applicant: LIVEDO CORPORATION, Ehime (JP)

(72) Inventors: Yuki Takahashi, Tokushima (JP); Shingo Takeda, Tokushima (JP)

(73) Assignee: LIVEDO CORPORATION, Ehime (JP)

( * ) Notice: Subject to any disclaimer, the term of this patent is extended or adjusted under 35 U.S.C. 154(b) by 293 days.

(21) Appl. No.: 18/286,432

(22) PCT Filed: Oct. 7, 2021

(86) PCT No.: PCT/JP2021/037122
§ 371 (c)(1),
(2) Date: Oct. 11, 2023

(87) PCT Pub. No.: WO2022/219832
PCT Pub. Date: Oct. 20, 2022

(65) Prior Publication Data
US 2024/0180760 A1    Jun. 6, 2024

(30) Foreign Application Priority Data

Apr. 12, 2021   (JP) ................................. 2021-067028

(51) Int. Cl.
*A61F 13/56*        (2006.01)
*A61F 13/532*       (2006.01)
(Continued)

(52) U.S. Cl.
CPC ........ *A61F 13/5611* (2013.01); *A61F 13/535* (2013.01); *A61F 2013/5147* (2013.01); *A61F 13/5323* (2013.01)

(58) Field of Classification Search
CPC .............. A61F 13/5323; A61F 13/5611; A61F 13/53418; A61F 13/532; A61F 13/535
See application file for complete search history.

(56) References Cited

U.S. PATENT DOCUMENTS

2004/0238393 A1* 12/2004 Ohi ...................... A61F 15/001
604/385.02
2006/0189954 A1  8/2006 Kudo et al.
(Continued)

FOREIGN PATENT DOCUMENTS

GB        2557151       6/2018
JP     2006-230596      9/2006
(Continued)

OTHER PUBLICATIONS

English language translation of International Preliminary Report on Patentability issued Oct. 12, 2023 in corresponding International (PCT) Patent Application No. PCT/JP2021/037122.
(Continued)

*Primary Examiner* — Susan S Su
(74) *Attorney, Agent, or Firm* — Wenderoth, Lind & Ponack, L.L.P.

(57)        ABSTRACT

An absorbent product includes an adhesive portion arranged on a surface of a back sheet opposite to a wearer side. Longitudinal-side boundary portions are between first and second areas of an absorber, the second area being thinner than the first area. The adhesive portion includes first adhesive elements and second adhesive elements arranged on the back sheet to avoid the longitudinal-side boundary portions. Each of the first adhesive elements extends in one of a longitudinal direction or a width direction in the first area, and the first adhesive elements are aligned in the other of the longitudinal direction or the width direction in the first area. Each of the second adhesive elements extends in one of a longitudinal direction or a width direction in the second area, and the second adhesive elements are aligned in the other of the longitudinal direction or the width direction in the second area.

5 Claims, 8 Drawing Sheets

(51) Int. Cl.
_A61F 13/535_ (2006.01)
_A61F 13/514_ (2006.01)

(56) References Cited

U.S. PATENT DOCUMENTS

| | | | |
|---|---|---|---|
| 2009/0062761 A1* | 3/2009 | Goerg-Wood ...... | A61F 13/5611 |
| | | | 604/385.01 |
| 2010/0121296 A1 | 5/2010 | Noda et al. | |
| 2018/0353353 A1* | 12/2018 | Konawa ................ | A61F 13/532 |

FOREIGN PATENT DOCUMENTS

| | | |
|---|---|---|
| JP | 2006-247088 | 9/2006 |
| JP | 2007-236552 | 9/2007 |
| JP | 2010-075315 | 4/2010 |
| JP | 2017-042471 | 3/2017 |
| JP | 2018-015463 | 2/2018 |
| JP | 2019-146916 | 9/2019 |
| JP | 2019-162526 | 9/2019 |
| WO | 2008/117755 | 10/2008 |
| WO | 2017/061566 | 4/2017 |
| WO | 2018/142824 | 8/2018 |
| WO | 2019/021444 | 1/2019 |

OTHER PUBLICATIONS

International Search Report issued Dec. 28, 2021 in International (PCT) Application No. PCT/JP2021/037122.

* cited by examiner

Fig. 5

ABSORBENT PRODUCT

CROSS-REFERENCE TO RELATED APPLICATION

This application claims the benefit of priority to Japanese Patent Application No. 2021-067028 filed on Apr. 12, 2021, the entire disclosure of which is incorporated herein by reference.

The present invention relates to an absorbent product for receiving body waste from the wearer.

BACKGROUND ART

Conventionally, absorbent products have been used, such as absorbent pads for light urinary incontinence that are secured to the inner sides of products such as underclothes or disposal diapers. Such an absorbent product includes a back sheet provided generally with an adhesive portion or the like for securing the absorbent product to the inner side of a product such as underclothes or a disposable diaper.

For example, the panty liner disclosed in Japanese Patent Application Publication No. 2010-075315 (hereinafter, "JP 2010-075315") includes a back sheet provided with, as anti-displacement measures, a rectangular adhesive portion that approximately overlaps the entire absorber formed of pulp fibers or any like material. The absorbent product disclosed in Japanese Patent Application Publication No. 2018-15463 (hereinafter, "JP 2018-15463") includes a strip adhesive portion that extends in either the longitudinal or width direction on a back sheet. The panty liner disclosed in Japanese Patent Application Publication No. 2006-247088 (hereinafter, "JP 2006-247088") reduces the formation of robust creases by arranging a strip adhesive portion that extends in either the longitudinal or width direction on a back sheet to avoid overlaps with folding lines in packaging in which the panty liner before use is folded. Those adhesive portions are formed by applying an adhesive or the like onto the back sheet during production of absorbent products.

By the way, if the adhesive portion is provided to approximately overlap the entire absorber as in JP 2010-075315, the absorbent product may have an excessively high strength to secure itself to a product such as underclothes or a disposable diaper (such a product is hereinafter also referred to as an "exterior product") and accordingly may become difficult to detach from the exterior product. In the absorbent product disclosed in JP 2018-15463, a relatively long slender strip of adhesive portion is arranged spanning both edges of the absorber. Thus, when the adhesive portion is formed by applying an adhesive or the like on the back sheet, twisting of the adhesive portion may occur. If the adhesive portion becomes twisted, it may become difficult to favorably secure the absorbent product to the inner side of an exterior product. In JP 2006-247088, no consideration is given to the relationship between the strip adhesive portion and the edges of the absorber.

Moreover, absorbent products as described above may also use an absorber having a two-layer structure. If the first layer and the second layer are different in size in plan view, a difference in level also occurs at the boundary portion between the first and second layers. JP 2010-075315, JP 2018-15463, and JP 2006-247088 give no consideration to the influence of such a small difference in level on the aforementioned twisting of the adhesive portion.

SUMMARY OF THE INVENTION

The present invention relates to an absorbent product for receiving body wastes from the wearer, and it is an object of the present invention to reduce the occurrence of twisting of adhesive elements.

An absorbent product according to one preferable embodiment of the present invention includes a liquid-permeable top sheet, a liquid-repellent or liquid-impermeable back sheet, an absorber arranged between the top sheet and the back sheet, and an adhesive portion provided on a surface of the back sheet on an opposite side to a wearer side. The absorber includes a first area located in a central portion in a longitudinal direction, a second area that is thinner than the first area and contiguous to the first area on both sides in the longitudinal direction of the first area, and a pair of longitudinal-side boundary portions that are boundary portions between the first area and the second area on both sides in the longitudinal direction of the first area. Each of the pair of longitudinal-side boundary portions extends in a width direction. The adhesive portion includes a plurality of adhesive elements arranged on the back sheet to avoid the pair of longitudinal-side boundary portions. The plurality of adhesive elements include a plurality of first adhesive elements each extending in either of the longitudinal direction and the width direction and aligned in the other of the longitudinal direction and the width direction in the first area, and a plurality of second adhesive elements each extending in either of the longitudinal direction and the width direction and aligned in the other of the longitudinal direction and the width direction in the second area.

According to the present invention, it is possible to reduce the occurrence of twisting of the adhesive elements.

Preferably, the absorber may include a first absorbent sheet that secures a particulate or fibrous high absorbent material to a main surface of a sheet support member with an adhesive, and a second absorbent sheet that is longer than the first absorbent sheet in the longitudinal direction and arranged between the first absorbent sheet and either of the back sheet and the top sheet. The first area of the absorber may be an area where the first absorbent sheet and the second absorbent sheet overlap each other in a thickness direction, and the second area of the absorber may be an area of the second absorbent sheet that extends outward from the first absorbent sheet.

Preferably, an interval of adhesive elements that are located between the pair of longitudinal-side boundary portions, among the plurality of adhesive elements, may be greater than an interval of adhesive elements that are located outward of the pair of longitudinal-side boundary portions in the longitudinal direction.

Preferably, the second area of the absorber may be also contiguous to the first area on both sides in the width direction of the first area. The absorber may further include a pair of lateral-side boundary portions that are boundary portions between the first area and the second area on both sides in the width direction of the first area. Each of the pair of lateral-side boundary portions extends in the longitudinal direction. The plurality of adhesive elements are arranged on the back sheet to avoid the pair of lateral-side boundary portions.

Preferably, a shortest distance in the width direction between each of the pair of lateral-side boundary portions and the plurality of first adhesive elements may be greater than or equal to 1 mm and less than or equal to 7.5 mm.

Preferably, the absorbent product before use may be folded along a folding line that extends in the width direction, and the plurality of adhesive elements may be arranged on the back sheet to avoid the folding line.

Preferably, a shortest distance in the longitudinal direction between the folding line and the plurality of first adhesive elements may be greater than a shortest distance in the longitudinal direction between each of the pair of longitudinal-side boundary portions and the plurality of first adhesive elements.

These and other objects, features, aspects and advantages of the present invention will become more apparent from the following detailed description of the present invention when taken in conjunction with the accompanying drawings.

BRIEF DESCRIPTION OF DRAWINGS

FIG. 5 is a bottom view of an absorbent product according to a third embodiment.

DESCRIPTION OF EMBODIMENTS

Figure 1:
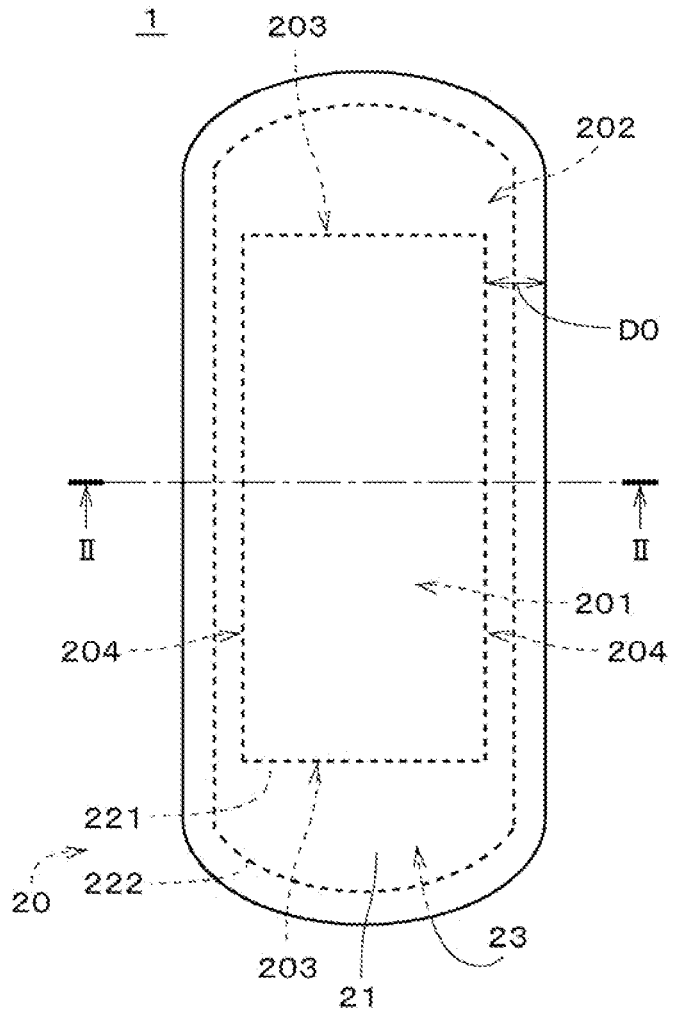
FIG. 1 is a plan view of an absorbent product according to a first embodiment.
Figures 2, 3:
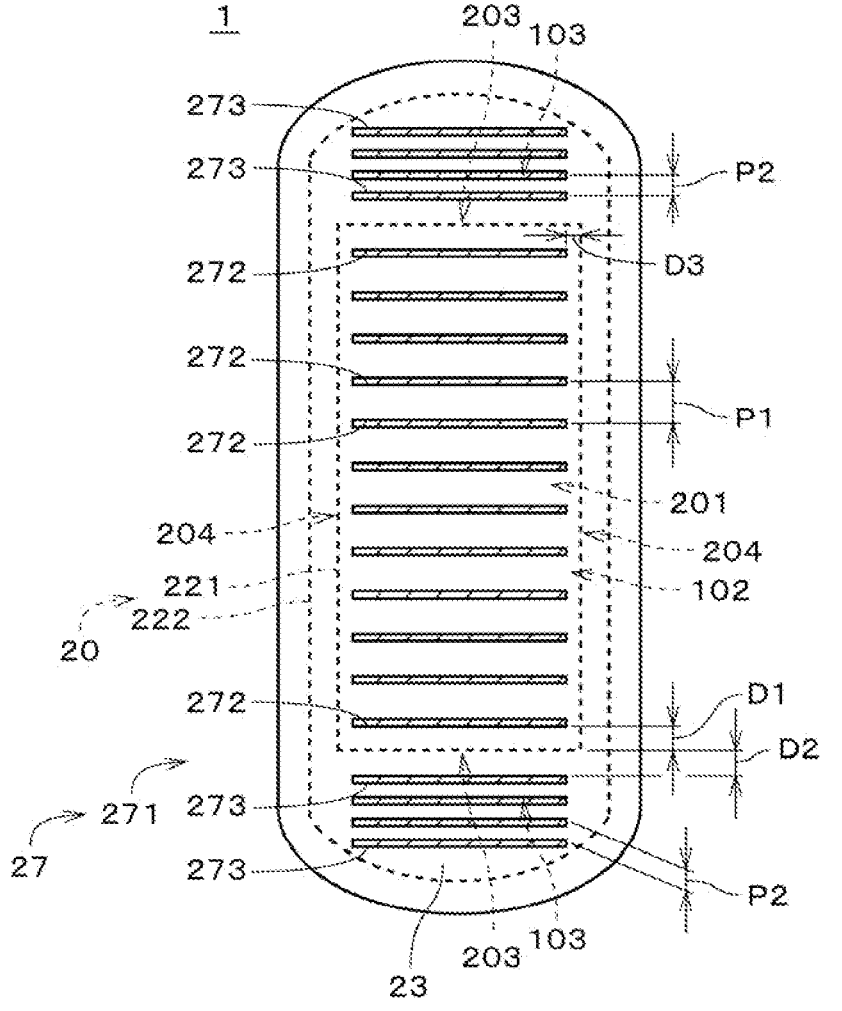
FIG. 2 is a sectional view of the absorbent product.
FIG. 3 is a bottom view of the absorbent product.

FIG. 1 is a plan view of an absorbent product 1 according to a first embodiment of the present invention. FIG. 2 is an enlarged view of a section of the absorbent product 1, taken at a position II-II in FIG. 1 along a plane perpendicular to the longitudinal direction (i.e., the up-down direction in FIG. 1). In the illustration in FIG. 2, the thickness of the absorbent product 1 in the thickness direction (i.e., the up-down direction in FIG. 2) is greater than the actual thickness. To facilitate understanding of the drawing, some constituent elements of the absorbent product 1 in FIG. 2 are illustrated apart from one another in the thickness direction, although they are actually in contact with one another.

The absorbent product 1 receives liquid body wastes such as urine from the wearer. For example, the absorbent product 1 may be an absorbent pad for light urinary incontinence that is secured to the inner side of an exterior product such as a disposable diaper or underclothes worn by the wearer for use. In FIG. 1, the absorbent product 1 is illustrated with a surface that comes in contact with the wearer (hereinafter, also referred to as the "upper surface") being oriented toward the front. In the example shown in FIG. 1, the absorbent product 1 has an approximately rectangular shape in plan view that has a greater length in the longitudinal direction than the width in the width direction (i.e., the right-left direction in FIG. 1). In the example shown in FIG. 1, both edges of the absorbent product 1 in the longitudinal direction have a convex shape. In the following description, the length of each area of the absorbent product 1 in the longitudinal direction is also simply referred to as the "length," and the width thereof in the width direction is also simply referred to as the "width." The thickness of each area of the absorbent product 1 in the thickness direction is also simply referred to as the "thickness." For example, the absorbent product 1 may have a length of 190 mm to 300 mm, a width of 70 mm to 170 mm, and a thickness of 1 mm to 6 mm.

As shown in FIGS. 1 and 2, the absorbent product 1 includes a liquid-permeable top sheet 21, a liquid-repellent or liquid-impermeable back sheet 23, an absorber 20, and an adhesive portion 27. The top sheet 21 is arranged on the upper side of the back sheet 23 (i.e., the wearer side). The absorber 20 is a sheet member arranged between the top sheet 21 and the back sheet 23. In FIG. 1, the contour of the absorber 20 (i.e., the contours of first and second absorbent sheets 221 and 222 described later) is indicated by thick broken lines to facilitate understanding of the drawing.

The shape of the top sheet 21 in plan view is approximately the same as the shape of the back sheet 23 in plan view. Outer edge portions of the top sheet 21 and the back sheet 23 are bonded together throughout the entire periphery of the absorber 20. The bonding of the outer edge portions of the top sheet 21 and the back sheet 23 is implemented by, for example, heat sealing and adhesion using an adhesive. The bonding may also be implemented by any of various methods (e.g., ultrasonic sealing) other than those described above.

The top sheet 21 is a liquid-permeable sheet member that quickly captures moisture in body wastes received from the wearer and passes the moisture to the absorber 20. Examples of the top sheet 21 include liquid-permeable nonwoven fabric (e.g., a point-bonded nonwoven fabric, an air-through nonwoven fabric, or a spun-bonding nonwoven fabric) formed of hydrophobic fibers (e.g. polypropylene, polyethylene, polyester, polyamide, or nylon) whose surfaces have undergone hydrophilic treatment using a surfactant. Other examples of the top sheet 21 include nonwoven fabric (e.g., a spun-lace nonwoven fabric) such as cellulose, rayon, or cotton.

The back sheet 23 is a liquid-repellent or liquid-impermeable sheet member that prevents moisture or the like in body wastes that have reached the back sheet 23 from leaking to the outside of the absorbent product 1. Examples of the back sheet 23 include liquid-repellent or liquid-impermeable nonwoven fabric or plastic film and a laminated sheet in which such nonwoven fabric and plastic film are laminated one above another. The nonwoven fabric used for the back sheet 23 may, for example, be a spun-bonding or melt-blown nonwoven fabric formed of hydrophobic fibers or a spun-bonded-melt blown-spun-bonded (SMS) nonwoven fabric and may be made liquid repellent as necessary. In the case of using a plastic film for the back sheet 23, it is preferable to use a plastic film having moisture permeability (air permeability) from the viewpoint of preventing stuffiness in the absorbent product 1 and improving comfortability of the wearer.

The absorber 20 includes a first absorbent sheet 221 and a second absorbent sheet 222. The first and second absorbent sheets 221 and 222 are sheet members. The first and second absorbent sheets 221 and 222 are laminated one above the other in the thickness direction. The second absorbent sheet 222 is arranged on the underside or the upper side of the first absorbent sheet 221. In other words, the second absorbent sheet 222 is arranged between the first absorbent sheet 221 and either of the back sheet 23 and the top sheet 21 in the thickness direction. In yet other words, the first absorbent sheet 221 is arranged between the second absorbent sheet 222 and either of the top sheet 21 and the back sheet 23 in the thickness direction. In the present embodiment, the second absorbent sheet 222 is arranged on the underside of the first absorbent sheet 221 (i.e., on the opposite side to the wearer).

In the example shown in FIG. 1, the first absorbent sheet 221 has an appropriately rectangular shape in plan view that is greater in length than width. The second absorbent sheet 222 is larger than the first absorbent sheet 221 and has an approximately rectangular shape in plan view that is greater in length than width. In the example illustrated in FIG. 1, both edges of the second absorbent sheet 222 in the longitudinal direction have a concave shape. In plan view, the outer edge of the second absorbent sheet 222 approximately overlaps the inner edge of the joint between the outer edge portions of the top sheet 21 and the back sheet 23.

In the example shown in FIG. 2, the first absorbent sheet 221 includes a first upper sheet 223, a high absorbent material 224, and a first lower sheet 225. The first lower sheet 225 is arranged under the first upper sheet 223 (i.e., on the opposite side to the wearer) and laminated on the first upper sheet 223 in the thickness direction. The first upper sheet 223 and the first lower sheet 225 are liquid-permeable sheet members. Examples of the first upper sheet 223 and the first lower sheet 225 include liquid permeable nonwoven fabric (e.g., a spun lace nonwoven fabric, an air-through nonwoven fabric, or a spun-bonding nonwoven fabric).

The high absorbent material 224 may, for example, be a particulate high absorbent material (super absorbent polymer: SAP) or a fibrous high absorbent material (super absorbent fiber: SAF). In the example shown in FIG. 2, SAP is used as the high absorbent material 224. In the illustration in FIG. 2, particles of the high absorbent material 224 are greater than their actual sizes. The high absorbent material 224 is arranged between the first upper sheet 223 and the first lower sheet 225 and secured with a hot-melt adhesive or the like (not shown) to at least one of the main surfaces of the first upper sheet 223 and the first lower sheet 225. That is, the first upper sheet 223 and the first lower sheet 225 are sheet support members that support the high absorbent material 224.

In the first absorbent sheet 221, the high absorbent material 224 is arranged in strips, each extending in the longitudinal direction. Specifically, the high absorbent material 224 is arranged in a plurality of material existence regions, each having an approximately rectangular band-like shape extending in the longitudinal direction. The material existence regions are aligned apart from one another in the width direction. The high absorbent material 224 does not exist substantially in regions between the material existence regions, so that in those regions, the first upper sheet 223 and the first lower sheet 225 are bonded together. The bonding of the first upper sheet 223 and the first lower sheet 225 may be implemented by, for example, embossing that involves heating.

The first absorbent sheet 221 absorbs and holds a liquid that has permeated through the top sheet 21. Specifically, the high absorbent material 224 of the first absorbent sheet 221 secures the liquid inside the first absorbent sheet 221 by absorbing the liquid and swelling. In the example shown in FIG. 2, a bulked absorptive material (e.g. pulp fibers) does not exist substantially between the first upper sheet 223 and the first lower sheet 225 of the first absorbent sheet 221. In other words, the first absorbent sheet 221 is a so-called "SAP sheet" that is substantially formed of only the first upper sheet 223, the first lower sheet 225, and the high absorbent material 224 that is SAP.

In the example shown in FIG. 2, the second absorbent sheet 222 may be liquid-absorptive paper or a sheet of hydrophilic nonwoven fabric. For example, the second absorbent sheet 222 may be a liquid-absorptive board such as tissue paper. The second absorbent sheet 222 is thinner than the first absorbent sheet 221. Specifically, the second absorbent sheet 222 has a smaller average thickness (i.e., an average value of thickness across the entire surface) than the first absorbent sheet 221. The second absorbent sheet 222 holds a liquid that has permeated through the first absorbent sheet 221 and diffuses the liquid in the longitudinal direction and the width direction. The liquid diffused by the second absorbent sheet 222 is absorbed and secured by the first absorbent sheet 221 that is in contact with the second absorbent sheet 222. The second absorbent sheet 222 may be secured with an adhesive or the like to the first lower sheet 225 of the first absorbent sheet 221, or may not be secured thereto.

In plan view, the second absorbent sheet 222 is longer in the longitudinal direction than the first absorbent sheet 221. The second absorbent sheet 222 is wider in the width direction than the first absorbent sheet 221 in plan view. In other words, the length and width of the second absorbent sheet 222 in plan view are respectively greater than the length and width of the first absorbent sheet 221 in plan view. Both longitudinal end portions of the second absorbent sheet 222 extend in the longitudinal direction from both longitudinal edges of the first absorbent sheet 221. Both crosswise end portions of the second absorbent sheet 222 extend in the width direction from both crosswise edges of the first absorbent sheet 221. In other words, the second absorbent sheet 222 extends outward from the edge of the first absorbent sheet 221 throughout the entire periphery of the first absorbent sheet 221.

In the following description, the area of the central portion of the absorber 20 in both of the longitudinal direction and the width direction where the first absorbent sheet 221 and the second absorbent sheet 222 overlap each other in the thickness direction is also referred to as a "first area 201." The area of the second absorbent sheet 222 that extends outward from the first absorbent sheet 221 is also referred to as a "second area 202." The second area 202 is thinner than the first area 201 in the thickness direction. The difference in thickness between the first area 201 and the second area 202 may be in the range of, for example, 0.5 mm to 5 mm.

The second area 202 is contiguous to the first area 201 on both longitudinal sides of the first area 201 and extends from the longitudinal edges of the first area 201 toward the longitudinal edges of the absorbent product 1. The second area 202 is also contiguous to the first area 201 on both crosswise sides of the first area 201 and extends from the crosswise edge (side edge) of the first area 201 toward the crosswise edge of the absorbent product 1. In the example shown in FIG. 1, the second area 202 is a frame-like area that surrounds the first area 201 throughout the entire periphery and that is contiguous to the first area 201 throughout the entire periphery of the first area 201.

In the following description, boundary portions between the first area 201 and the second area 202 at the longitudinal ends of the first area 201 are referred to as "longitudinal-side boundary portions 203." Boundary portions between the first area 201 and the second area 202 at the crosswise ends of the first area 201 are referred to as "lateral-side boundary portions 204." The absorber 20 includes a pair of longitudinal-side boundary portions 203 on both sides in the longitudinal direction of the first area 201, and a pair of lateral-side boundary portions 204 on both sides in the width direction of the first area 201. Each of the pair of longitudinal-side boundary portions 203 extends in the width direction. Each of the pair of lateral-side boundary portions 204 extends in the longitudinal direction.

In the example shown in FIG. 1, the longitudinal-side boundary portions 203 are approximately linear areas that extend in approximately parallel with the width direction. Note that the longitudinal-side boundary portions 203 do not necessarily have to be approximately parallel to the width direction and, for example, may extend in a concave curve in the width direction or extend linearly in a direction inclined to the width direction. The longitudinal-side boundary portions 203 do not necessarily have to be linear areas, and may be band-like areas having a width to some extent (e.g., a width of approximately 1 mm to 2 mm) in the longitudinal direction.

In the example shown in FIG. 1, the lateral-side boundary portions 204 are approximately linear areas that extend in approximately parallel with the longitudinal direction. The lateral-side boundary portions 204 are approximately parallel to the side edges of the absorbent product 1 (i.e., the side edges of the back sheet 23), and a distance DO in the width direction between each lateral-side boundary portion 204 and one side edge of the absorbent product 1 that is closer to this lateral-side boundary portion 204 may be in the range of, for example, 5 mm to 20 mm. If the distance D0 is set to be greater than or equal to 5 mm, it is possible to ensure a sufficient width for the joint between the top sheet 21 and the back sheet 23 in the side end portions of the absorbent product 1. If the distance D0 is set to be less than or equal to 20 mm, it is possible to increase the width of the first absorbent sheet 221.

Note that the lateral-side boundary portions 204 do not necessarily have to be approximately parallel to the longitudinal direction and, for example, may extend in a concave curve in the longitudinal direction or extend linearly in a direction inclined to the longitudinal direction. Moreover, the lateral-side boundary portions 204 do not necessarily have to be linear areas, and may be band-like areas having a width to some extent (e.g., a width of approximately 1 mm to 2 mm) in the width direction.

FIG. 3 is a bottom view showing the opposite side of the absorbent product 1 to the wearer. In FIG. 3, the adhesive portion 27 on the lower surface of the back sheet 23 (i.e., the surface on the opposite side to the wearer) are cross-hatched to facilitate understanding of the drawing (the same applies to FIGS. 4, 5, 9, and 10). The adhesive portion 27 is a member for anti-displacement of the absorbent product 1 relative to the exterior product. When the adhesive portion 27 sticks to the inner surface of the exterior product (i.e., the surface on the wearer side), the absorbent product 1 is detachably secured to the inner side (i.e., the wearer side) of the exterior product. In FIG. 3, the contours of the first and second absorbent sheets 221 and 222 of the absorber 20 are indicated by thick broken lines (the same applies to FIGS. 4, 5, 9, and 10).

The adhesive portion 27 includes a plurality of adhesive elements 271 each extending in the width direction and aligned in the longitudinal direction. In the example shown in FIG. 3, each adhesive element 271 has an approximately rectangular band-like shape that extends approximately linearly in approximately parallel with the width direction. The adhesive elements 271 have approximately the same shape. The magnitude of each adhesive element 271 in the width direction may be in the range of, for example, 30 mm to 120 mm, and the magnitude thereof in the longitudinal direction may be in the range of, for example, 1 mm to 10 mm. The thickness of each adhesive element 271 in the thickness direction may be in the range of, for example, 0.03 mm to 0.05 mm. The magnitudes and thickness of each adhesive element 271 are not limited to the ranges described above, and may be modified in various ways.

Each adhesive element 271 may be a relatively thin layer formed of, for example, a pressure-sensitive adhesive. The pressure-sensitive adhesive may, for example, be a rubber-based hot-melt adhesive. The adhesive portion 27 is formed by applying the pressure-sensitive adhesive in strips, each extending in the width direction, on the back sheet 23 by a coater or any other device. The amount of application of the pressure-sensitive adhesive may be in the range of, for example, 40 g/m$^2$ to 60 g/m$^2$. Note that the type of the adhesive used to form the adhesive elements 271 and the amount of application of the adhesive may be modified in various ways. Moreover, the adhesive elements 271 may be formed of a material other than the adhesive.

The adhesive elements 271 are arranged on the back sheet 23 to avoid the aforementioned pair of longitudinal-side boundary portions 203. In other words, the adhesive portion 27 is configured by the adhesive elements 271 that are arranged on the back sheet 23 to avoid the pair of longitudinal-side boundary portions 203. The adhesive elements 271 on the back sheet 23 are also arranged to avoid the aforementioned pair of lateral-side boundary portions 204. In other words, the adhesive portion 27 is configured by the adhesive elements 271 that are arranged on the back sheet 23 to avoid the pair of lateral-side boundary portions 204. That is, each adhesive element 271 is arranged on the back sheet 23 so as to neither intersect with nor overlap any of the longitudinal-side boundary portions 203 and the lateral-side boundary portions 204 in plan view (i.e., in the thickness direction).

In the following description, a region of the absorbent product 1 that is located between the pair of longitudinal-side boundary portions 203 in the longitudinal direction is also referred to as a "longitudinal central region 102," and adhesive elements 271 that are located in the longitudinal central region 102 are also referred to as "central adhesive elements 272." Moreover, two regions of the absorbent product 1 that are located outside the pair of longitudinal-side boundary portions 203 in the longitudinal direction (i.e., the regions other than the longitudinal central region 102) are also referred to as "longitudinal end regions 103," and adhesive elements 271 that are located in the longitudinal end regions 103 are also referred to as "end adhesive elements 273." Each longitudinal end region 103 is a region that is located on the side closer to the end portion of the absorbent product 1 in the longitudinal direction than the longitudinal-side boundary portion 203. Among the adhesive elements 271, the end adhesive elements 273 are adhesive elements 271 other than the central adhesive elements 272. As shown in FIG. 3, the adhesive elements 271 are arranged on both longitudinal sides of each longitudinal-side boundary portion 203 to avoid the pair of longitudinal-side boundary portions 203.

As described above, the adhesive elements 271 are arranged to avoid the lateral-side boundary portions 204 of the absorber 20. In the example shown in FIG. 3, the central adhesive elements 272 are spaced at an interval from one another and arranged inward in the width direction of and between the pair of lateral-side boundary portions 204. That is, the central adhesive elements 272 as a whole overlap the first absorbent sheet 221 in plan view. In other words, the central adhesive elements 272 as a whole are located on the first area 201 of the absorbent product 1. When, among the adhesive elements 271, those that are located on the first area 201 are referred to as "first adhesive elements," all of the central adhesive elements 272 in the example shown in FIG. 3 are the first adhesive elements. When, among the adhesive elements 271, those that are located on the second area 202 are referred to as "second adhesive elements," all of the adhesive elements 273 in the example shown in FIG. 3 are the second adhesive elements.

In the example shown in FIG. 3, the central adhesive elements 272, each extending in the width direction, are aligned and spaced at approximately a regular interval in the longitudinal direction on the longitudinal central region 102. In each longitudinal end region 103, the end adhesive elements 273, each extending in the width direction, are aligned and spaced at approximately a regular interval in the longitudinal direction. The interval of the central adhesive elements 272 refers to a distance in the longitudinal direction between the center lines of two central adhesive elements 272 that are adjacent to each other in the longitudinal direction (i.e., virtual lines extending in parallel with the width direction in the centers of the central adhesive elements 272 in the longitudinal direction). Similarly, the interval of the end adhesive elements 273 refers to a distance in the longitudinal direction between the center lines of two end adhesive elements 273 that are adjacent to each other in the longitudinal direction. Almost the same applies to the intervals of the other adhesive elements, which will be described later.

The central adhesive elements 272 have approximately the same shape. The end adhesive elements 273 located in one of the two longitudinal end regions 103 and the end adhesive elements 273 located in the other longitudinal end region 103 are approximately the same in number, shape, and interval. The end adhesive elements 273 located in each longitudinal end region 103 and the central adhesive elements 272 located in the longitudinal central region 102 are approximately the same in shape as the adhesive elements 271.

An interval P1 in the longitudinal direction of the central adhesive elements 272 may, for example, be greater than an interval P2 in the longitudinal direction of the end adhesive elements 273 located in the two longitudinal end regions 103. This suppresses an excess increase in the strength to secure the longitudinal central portion of the absorbent product 1 to the exterior product and allows the longitudinal end portions of the absorbent product 1 to be firmly secured to the exterior product. As a result, it is possible to favorably reduce the occurrence of detachment or twisting of the absorbent product 1 secured to the inner side of the exterior product. Besides, the used absorbent product 1 can be detached with ease from the exterior product.

The interval P1 in the longitudinal direction of the central adhesive elements 272 may be in the range of, for example, 1 mm to 100 mm. If the interval P1 is set to be greater than or equal to 1 mm, it is possible to prevent an excessive increase in the strength to secure the absorbent product 1 to the exterior product in the longitudinal central region 102. If the interval P1 is set to be less than or equal to 100 mm, it is possible to reduce the possibility that the strength to secure the absorbent product 1 to the exterior product may become insufficient in the longitudinal central region 102. In other words, if the interval P1 is set to be in the range of 1 mm to 100 mm, the strength to secure the absorbent product 1 to the exterior product in the longitudinal central region 102 can fall within a favorable range.

The interval P2 in the longitudinal direction of the end adhesive elements 273 may be in the range of, for example, 1 mm to 15 mm. Accordingly, the strength to secure the absorbent product 1 to the exterior product in each longitudinal end region 103 can fall within a favorable range. Note that the intervals P1 and P2 are not limited to the ranges described above, and may be modified in various ways.

In the absorbent product 1, the central adhesive elements 272 and the end adhesive elements 273 do not necessarily have to be aligned at regular intervals. In the case where the central adhesive elements 272 are aligned at an irregular interval, the interval P1 in the longitudinal direction of the central adhesive elements 272 indicates an arithmetical mean (i.e., average interval) of shortest distances in the longitudinal direction between each pair of central adhesive elements 272 that are adjacent to each other in the longitudinal direction in the longitudinal central region 102. In the case where the end adhesive elements 273 are aligned at an irregular interval, the interval P2 in the longitudinal direction of the end adhesive elements 273 indicates an arithmetical mean of shortest distances in the longitudinal direction between each pair of end adhesive elements 273 that are adjacent to each other in the longitudinal direction in the two longitudinal end regions 103. The same applies to the intervals of the other adhesive elements, which will be described later.

As described above, the adhesive elements 271 are arranged to avoid the longitudinal-side boundary portions 203 of the absorber 20. In other words, the central adhesive elements 272 and the end adhesive elements 273 are arranged away from the longitudinal-side boundary portions 203 in the longitudinal direction. A shortest distance D1 (hereinafter, also referred to as an "alienation distance D1") in the longitudinal direction between one of the longitudinal-side boundary portions 203 and one central adhesive element 272 that is closest to this longitudinal-side boundary portion 203 in the longitudinal direction, among the central adhesive elements 272, may be in the range of, for example, 1 mm to 50 mm. If the alienation distance D1 between the central adhesive element 272 and the longitudinal-side boundary portion 203 is set to be greater than or equal to 1 mm, it is possible to reduce the occurrence of twisting of the central adhesive element 272 caused by the influences of a difference in level at the longitudinal-side boundary portion 203 (i.e., a difference in level caused by the difference in thickness between the first area 201 and the second area 202) in cases such as where the adhesive portion 27 is formed on the back sheet 23. If the alienation distance D1 is set to be less than or equal to 50 mm, it is possible to reduce the possibility that the strength to secure the absorbent product 1 to the exterior product may become insufficient in the vicinity of the longitudinal-side boundary portion 203.

In each longitudinal end region 103, a shortest distance D2 (hereinafter, also referred to as an "alienation distance D2") in the longitudinal direction between the longitudinal-side boundary portion 203 and one end adhesive element 273 that is closest to this longitudinal-side boundary portion 203 in the longitudinal direction, among the end adhesive elements 273, may be in the range of, for example, 1 mm to 10 mm. If the alienation distance D2 between the end adhesive element 273 and the longitudinal-side boundary portion 203 is set to be greater than or equal to 1 mm, it is possible to reduce the occurrence of twisting of the end adhesive element 273 caused by the influences of a difference in level at the longitudinal-side boundary portion 203 in cases such as where the adhesive portion 27 is formed on the back sheet 23. If the alienation distance D2 is set to be less than or equal to 10 mm, it is possible to reduce the possibility that the strength to secure the absorbent product 1 to the exterior product may become insufficient in the vicinity of the longitudinal-side boundary portion 203.

The alienation distances D1 and D2 may be approximately the same, or one of them may be greater than the other. The alienation distance D2 between the end adhesive element 273 and the longitudinal-side boundary portion 203 is greater than the interval P2 of the end adhesive elements 273. This reduces the occurrence of twisting of the end adhesive elements 273 in cases such as where the adhesive portion 27 is formed, and increases the strength to secure the absorbent product 1 to the exterior product in the longitudinal end region 103. As a result, it is possible to more firmly secure the longitudinal end portions of the absorbent product 1 to the exterior product and to prevent the occurrence of detachment or twisting of the absorbent product 1 secured to the inner side of the exterior product.

A shortest distance D3 (hereinafter, also referred to as an "alienation distance D3") in the width direction between the crosswise ends of the central adhesive elements 272 and the lateral-side boundary portion 204 that is closer to those ends may be in the range of, for example, 1 mm to 7.5 mm. If the alienation distance D3 between the central adhesive elements 272 and the lateral-side boundary portion 204 is set to be greater than or equal to 1 mm, it is possible to reduce the occurrence of twisting of the crosswise ends of the central adhesive elements 272 caused by the influences of a difference in level at the lateral-side boundary portion 204 (i.e., a difference in level caused by the difference in thickness between the first area 201 and the second area 202) in cases such as where the adhesive portion 27 is formed on the back sheet 23. If the alienation distance D3 is set to be less than or equal to 7.5 mm, it is possible to reduce the possibility that the strength to secure the absorbent product 1 to the exterior product may become insufficient in the vicinity of the lateral-side boundary portion 204.

In the example shown in FIG. 3, the central adhesive elements 272 are not provided outside the pair of lateral-side boundary portions 204 in the width direction in the longitudinal central region 102 of the absorbent product 1. In other words, in the longitudinal central region 102, the central adhesive elements 272 are provided only on the area that overlaps the first absorbent sheet 221 in plan view (i.e., only on the first area 201), and the adhesive elements 271 are not provided substantially on the area that does not overlap the first absorbent sheet 221 in plan view. This suppresses an excessive increase in the strength to secure the longitudinal central portion of the absorbent product 1 to the exterior product.

Figure 4:
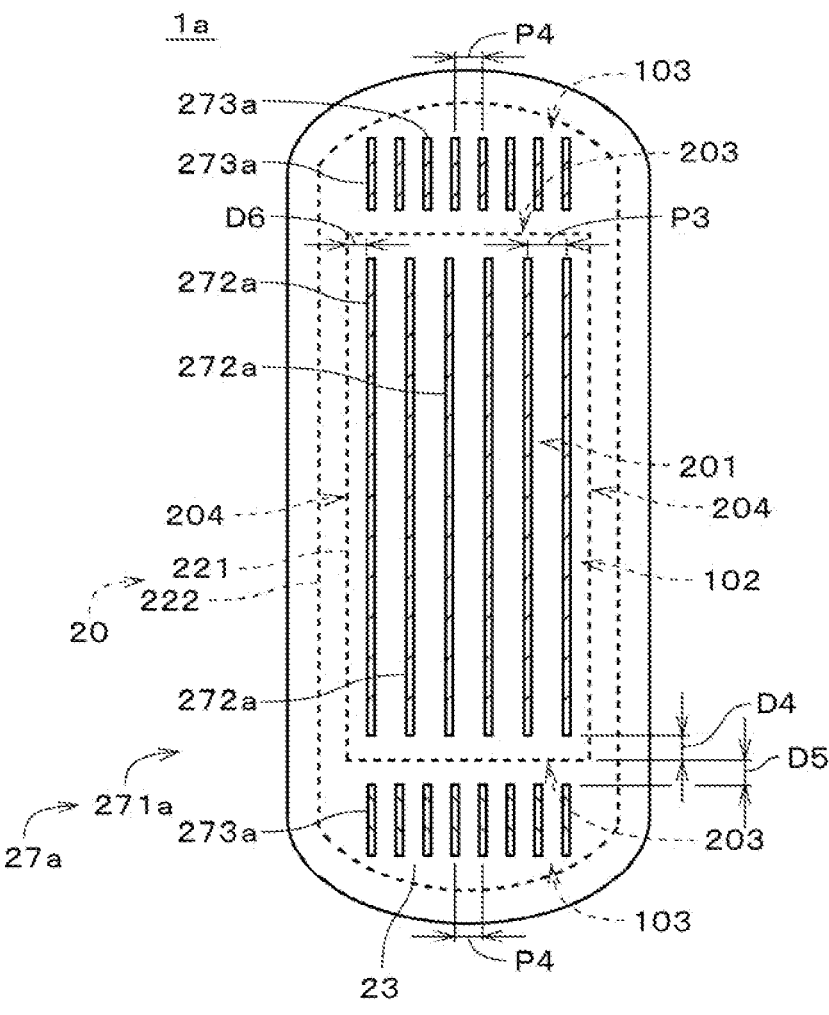
FIG. 4 is a bottom view of an absorbent product according to a second embodiment.

FIG. 4 is a bottom view showing an absorbent product 1a according to a second embodiment of the present invention. The absorbent product 1a has an approximately similar structure to that of the absorbent product 1 described above, except that an adhesive portion 27a that is different in shape from the adhesive portion 27 shown in FIG. 3 is provided on the back sheet 23. In the following description, the other constituent elements of the absorbent product 1a are given the same reference signs as the corresponding constituent elements of the absorbent product 1 shown in FIGS. 1 to 3.

As shown in FIG. 4, the adhesive portion 27a of the absorbent product 1a includes a plurality of adhesive elements 271a each extending in the longitudinal direction and aligned in the width direction. In the example shown in FIG. 4, each adhesive element 271a has an approximately rectangular band-like shape that extends approximately linearly in approximately parallel with the longitudinal direction. The adhesive elements 271a are arranged on the back sheet 23 to avoid the pair of longitudinal-side boundary portions 203. The adhesive elements 271a on the back sheet 23 are also arranged to avoid the pair of lateral-side boundary portions 204. In other words, each adhesive element 271a is arranged on the back sheet 23 so as to neither intersect with nor overlap any of the longitudinal-side boundary portions 203 and the lateral-side boundary portions 204 in plan view (i.e., in the thickness direction).

In the example shown in FIG. 4, a plurality of central adhesive elements 272a that are arranged in the longitudinal central region 102, among the adhesive elements 271a, are located between the pair of longitudinal-side boundary portions 203 in the longitudinal direction and between the pair of lateral-side boundary portions 204 in the width direction. That is, the central adhesive elements 272a as a whole overlap the first absorbent sheet 221 in plan view. In other words, the central adhesive elements 272a as a whole are located on the first area 201 of the absorbent product 1a. When, among the adhesive elements 271a, those that are located on the first area 201 are referred to as "first adhesive elements," all of the central adhesive elements 272a in the example shown in FIG. 4 are the first adhesive elements. When, among the adhesive elements 271a, those that are located on the second area 202 are referred to as "second adhesive elements," all of a plurality of end adhesive elements 273a in the example shown in FIG. 4 are the second adhesive elements.

The central adhesive elements 272a, each extending in the longitudinal direction, are aligned and spaced from one another at approximately a regular interval in the width direction. The central adhesive elements 272a have approximately the same shape. The length of each central adhesive element 272a in the longitudinal direction may be in the range of, for example, 110 mm to 230 mm, and the width thereof in the width direction may be in the range of, for example, 1 mm to 10 mm. The thickness of central adhesive element 272a in the thickness direction may be in the range of, for example, 0.03 mm to 0.05 mm. The magnitudes and thickness of the central adhesive elements 272a are not limited to the ranges described above, and may be modified in various ways.

Among the adhesive elements 271a, the end adhesive elements 273a located in each longitudinal end region 103 each extend in the longitudinal direction and are arranged and spaced from one another at approximately a regular interval in the width direction. The end adhesive elements 273a located in each longitudinal end region 103 have approximately the same shape. The end adhesive elements 273a located in one of the two longitudinal end regions 103 and the end adhesive elements 273a located in the other longitudinal end region 103 are approximately the same in number, shape, and interval. The length of each end adhesive element 273a in the longitudinal direction may be in the range of, for example, 5 mm to 25 mm, and the width thereof in the width direction may be in the range of, for example, 1 mm to 10 mm. The thickness of each end adhesive element 273a in the thickness direction may be in the range of, for example, 0.03 mm to 0.05 mm. The magnitudes and thickness of the adhesive elements 273a are not limited to the ranges described above, and may be modified in various ways.

An interval P3 in the width direction of the central adhesive elements 272a may, for example, be greater than an interval P4 in the width direction of the end adhesive elements 273a located in the two longitudinal end regions 103. This suppresses an excessive increase in the strength to secure the longitudinal central portion of the absorbent product 1a to the exterior product and allows the longitudinal end portions of the absorbent product 1a to be firmly secured to the exterior product. As a result, it is possible to favorably reduce the occurrence of detachment or twisting of the absorbent product 1a secured to the inner side of the exterior product. Besides, the used absorbent product 1a can be detached with ease from the exterior product.

The interval P3 in the width direction of the central adhesive elements 272a may be in the range of, for example, 1 mm to 100 mm. Accordingly, the strength to secure the absorbent product 1a to the exterior product in the longitudinal central region 102 can fall within a favorable range. The interval P4 in the width direction of the end adhesive elements 273a may be in the range of, for example, 1 mm to 15 mm. Accordingly, the strength to secure the absorbent product 1a to the exterior product in each longitudinal end region 103 can fall within a favorable range. Note that the intervals P3 and P4 are not limited to the ranges described above, and may be modified in various ways.

A shortest distance D4 (hereinafter, also referred to as an "alienation distance D4") in the longitudinal direction between one longitudinal ends of the central adhesive elements 272a and the longitudinal-side boundary portion 203 that is closer to these ends may be in the range of, for example, 1 mm to 50 mm. This reduces the occurrence of twisting of the longitudinal ends of the central adhesive elements 272a caused by the influences of a difference in level at the longitudinal-side boundary portion 203 in cases such as where the adhesive portion 27a is formed on the back sheet 23, and also reduces the possibility that the strength to secure the absorbent product 1a to the exterior product may become insufficient in the vicinity of the longitudinal-side boundary portion 203.

In each longitudinal end region 103, a shortest distance D5 (hereinafter, also referred to as an "alienation distance D5") in the longitudinal direction between the longitudinal ends of the end adhesive elements 273a and the longitudinal-side boundary portion 203 that is closer to these ends may be in the range of, for example, 1 mm to 10 mm. This reduces the occurrence of twisting of the longitudinal ends of the end adhesive elements 273a caused by the influences of a difference in level at the longitudinal-side boundary portion 203 in cases such as where the adhesive portion 27a is formed on the back sheet 23, and also reduces the possibility that the strength to secure the absorbent product 1a to the exterior product may become insufficient in the vicinity of the longitudinal-side boundary portion 203. The alienation distances D4 and D5 may be approximately the same, or one of them may be greater than the other.

A shortest distance D6 (hereinafter, also referred to as an "alienation distance D6") in the width direction between one lateral-side boundary portion 204 and one central adhesive element 272a that is closest to this lateral-side boundary portion 204, among the central adhesive elements 272a, may be in the range of, for example, 1 mm to 7.5 mm. If the alienation distance D6 between the central adhesive element 272a and the lateral-side boundary portion 204 is set to be greater than or equal to 1 mm, it is possible to reduce the occurrence of twisting of the central adhesive elements 272a caused by the influences of a difference in level at the lateral-side boundary portion 204 in cases such as where the adhesive portion 27a is formed on the back sheet 23. If the alienation distance D6 is set to be less than or equal to 7.5 mm, it is possible to reduce the possibility that the strength to secure the absorbent product 1a to the exterior product may become insufficient in the vicinity of the lateral-side boundary portion 204.

In the example shown in FIG. 4, the central adhesive elements 272a are not provided outside the pair of lateral-side boundary portions 204 in the width direction in the longitudinal central region 102 of the absorbent product 1a. In other words, in the longitudinal central region 102, the central adhesive elements 272a are provided only on the area that overlaps the first absorbent sheet 221 in plan view (i.e., only on the first area 201), and the adhesive elements 271a are not provided substantially on the area that does not overlap the first absorbent sheet 221 in plan view. This suppresses an excessive increase in the strength to secure the longitudinal central portion of the absorbent product 1a to the exterior product.

As described above, the absorbent product 1 or 1a for receiving body wastes from the wearer includes the liquid-permeable top sheet 21, the liquid-repellent or liquid-impermeable back sheet 23, the absorber 20, and the adhesive portion 27 or 27a. The absorber 20 is arranged between the top sheet 21 and the back sheet 23. The adhesive portion 27 or 27a is provided on the surface of the back sheet 23 on the opposite side to the wearer side. The absorber 20 includes the first area 201, the second area 202, and the pair of longitudinal-side boundary portions 203. The first area 201 is located in the longitudinal central portion of the absorber 20. The second area 202 is contiguous to the first area 201 on both sides in the longitudinal direction of the first area 201. The second area 202 is thinner than the first area 201. The pair of longitudinal-side boundary portions 203 are boundary portions between the first area 201 and the second area 202 on both sides in the longitudinal direction of the first area 201. Each of the pair of longitudinal-side boundary portions 203 extends in the width direction.

The adhesive portion 27 or 27a is configured by the adhesive elements 271 or 271a that are arranged on the back sheet 23 to avoid the pair of longitudinal-side boundary portions 203. The adhesive elements 271 or 271a include the first adhesive elements (in the above-described example, the central adhesive elements 272 or 272a) and the second adhesive elements (in the above-described example, the end adhesive elements 273 or 273a). The first adhesive elements each extend in one of the longitudinal direction and the width direction in the first area 201 and are aligned in the other of the longitudinal direction and the width direction. The second adhesive elements each extend in one of the longitudinal direction and the width direction in the second area 202 and are aligned in the other of the longitudinal direction and the width direction. This reduces the occurrence of twisting of the adhesive elements 271 or 271a caused by the influences of a difference in level at the longitudinal-side boundary portions 203 in cases such as where the adhesive portion 27 or 27a is formed on the back sheet 23. As a result, the absorbent product 1 or 1a can be favorably secured to the exterior product.

As described above, the absorber 20 may preferably include the first absorbent sheet 221 and the second absorbent sheet 222. The first absorbent sheet 221 may preferably be a member that secures the particulate or fibrous high absorbent material 224 with an adhesive to the main surface of the sheet support member (in the above-described example, the first upper sheet 223 and/or the first lower sheet 225). The second absorbent sheet 222 may preferably be a sheet member that is longer than the first absorbent sheet 221 in the longitudinal direction and arranged between the first absorbent sheet 221 and either of the back sheet 23 and the top sheet 21. The first area 201 of the absorber 20 is the area where the first and second absorbent sheets 221 and 222 overlap each other in the thickness direction. The second area 202 of the absorber 20 is the area of the second absorbent sheet 222 that extends outward from the first absorbent sheet 221. This reduces the occurrence of twisting of the adhesive elements 271 or 271*a* caused by the influences of a difference in level at the longitudinal-side boundary portions 203 in the slim absorbent product 1 or 1*a*.

As described above, the intervals P1 and P3 of the adhesive elements (i.e., the central adhesive elements 272 or 272*a*) between the pair of longitudinal-side boundary portions 203 may preferably be greater than the intervals P2 and P4 of the adhesive elements (i.e., the end adhesive elements 273 or 273*a*) outside the pair of longitudinal-side boundary portions 203 in the longitudinal direction. This suppresses an excessive increase in the strength to secure the longitudinal central portion of the absorbent product 1 or 1*a* to the exterior product and allows the longitudinal end portions of the absorbent produce 1 or 1*a* to be firmly secured to the exterior product. As a result, it is possible to favorably suppress the occurrence of detachment or twisting of the absorbent product 1 or 1*a* secured to the inner side of the exterior product. Moreover, the used absorbent product 1 or 1*a* can be detached with ease from the exterior product.

As described above, it is preferable that the second area 202 of the absorber 20 is also contiguous to the first area 201 on both sides in the width direction of the first area 201. The absorber 20 further includes the pair of lateral-side boundary portions 204 that are boundary portions between the first area 201 and the second area 202 on both sides in the width direction of the first area 201. Each of the pair of lateral-side boundary portions 204 extends in the longitudinal direction. It is preferable that the adhesive elements 271 or 271*a* may be arranged on the back sheet 23 to avoid the pair of lateral-side boundary portions 204. This reduces the occurrence of twisting of the adhesive elements 271 or 271*a* caused by the influences of a difference in level at the lateral-side boundary portions 204 in cases such as where the adhesive portion 27 or 27*a* is formed on the back sheet 23. As a result, it is possible to more favorably secure the absorbent product 1 or 1*a* to the exterior product.

As described above, it is preferable that the shortest distances D3 and D6 in the width direction between each of the pair of lateral-side boundary portions 204 and the aforementioned first adhesive elements (in the above-described example, the central adhesive elements 272 or 272*a*) may preferably be greater than or equal to 1 mm and less than or equal to 7.5 mm. This favorably reduces the occurrence of twisting of the adhesive elements 271 or 271*a* caused by the influences of a difference in level at the lateral-side boundary portions 204. Besides, it is possible to reduce the possibility that the strength to secure the absorbent product 1 or 1*a* to the exterior product may become insufficient in the vicinity of the lateral-side boundary portions 204.

Figure 5:
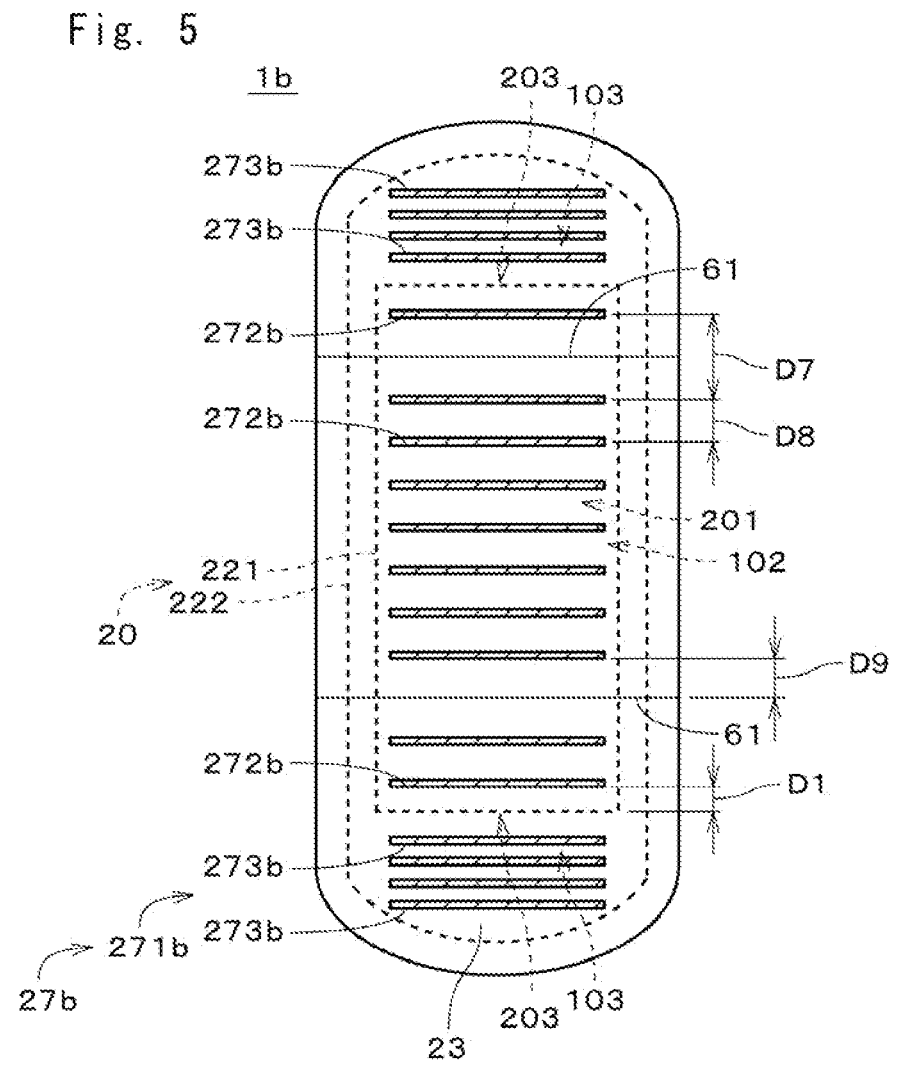

FIG. 5 is a bottom view of an absorbent product 1*b* according to a third embodiment of the present invention. The absorbent product 1*b* has an approximately similar structure to that of the absorbent product 1 described above, except that an adhesive portion 27*b* that is different in shape from the adhesive portion 27 shown in FIG. 3 is provided on the back sheet 23. In the following description, the other constituent elements of the absorbent product 1*b* are given the same reference signs as the corresponding constituent elements of the absorbent product 1 shown in FIGS. 1 to 3.

Figure 6:
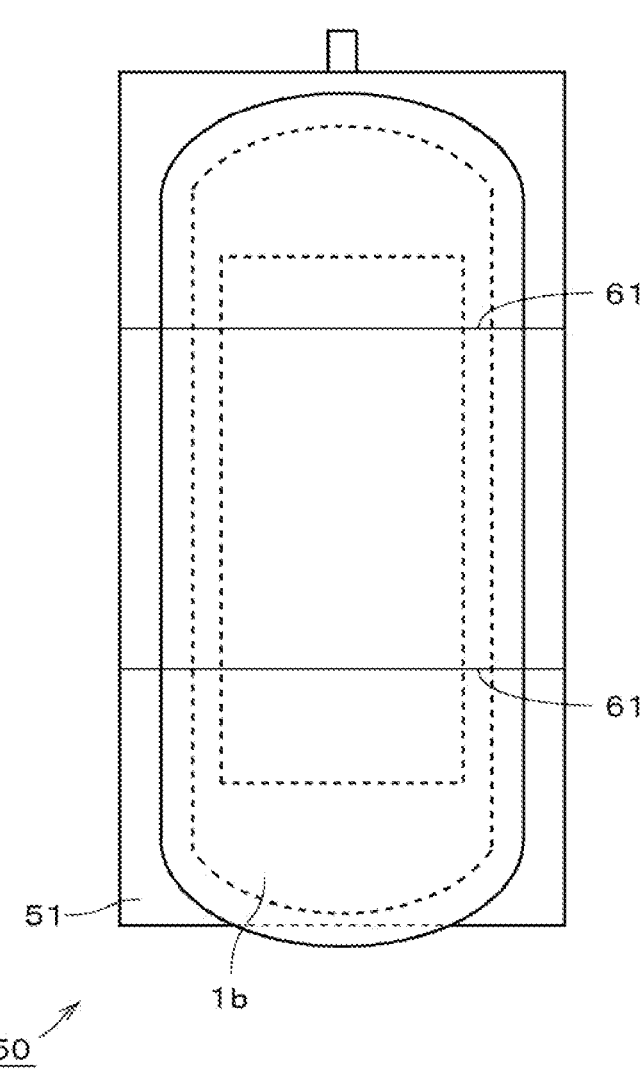
FIG. 6 is a plan view of an absorbent product and a packaging sheet.

FIG. 6 is a plan view showing the absorbent product 1*b* and a packaging sheet 51 together. The packaging sheet 51 is a sheet member used for individual packaging of the absorbent product 1*b*. For example, the packaging sheet 51 may be formed of a liquid-repellent or liquid-impermeable plastic film. The packaging sheet 51 is detachably secured to the absorbent product 1*b* with the adhesive portion 27*b* (see FIG. 5). The packaging sheet 51 has a greater width than the absorbent product 1*b*. The length of the packaging sheet 51 is approximately equal to the length of the absorbent product 1*b*. In the following description, the absorbent product 1*b* and the packaging sheet 51 are also collectively referred to as a "packaged absorbent product 50."

Figure 7:
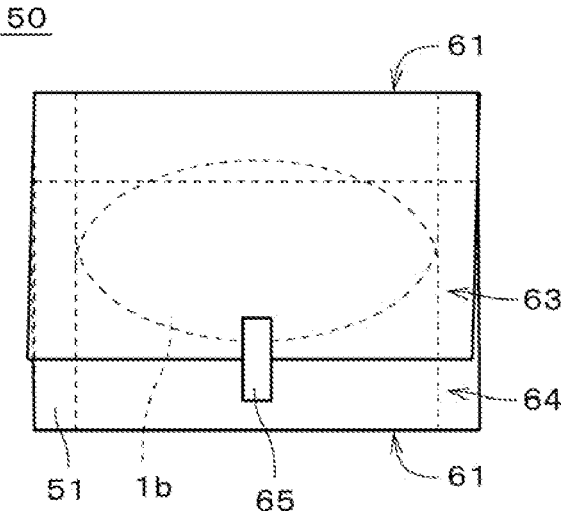
FIG. 7 is a plan view of a packaged absorbent product.
Figure 8:
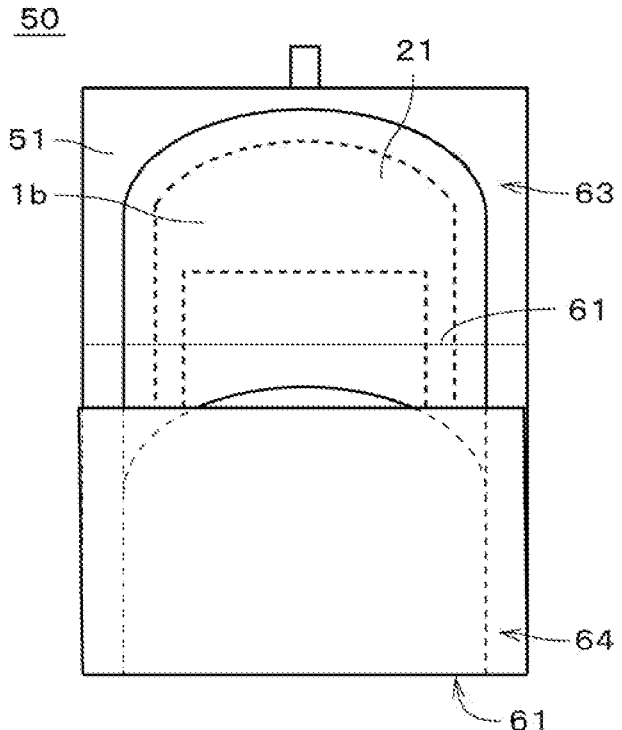
FIG. 8 is a developed view of part of the packaged absorbent product.

FIG. 7 is a plan view of the packaged absorbent product 50 before use. FIG. 8 is a plan view showing a developed state of part of the packaged absorbent product 50 shown in FIG. 7. As shown in FIG. 7, in the packaged absorbent product 50 before use, the packaging sheet 51 and the absorbent product 1*b* are folded into an orientation such that the top sheet 21 of the absorbent product 1*b* faces itself, along two folding lines 61 each extending in the width direction.

FIG. 8 shows a developed state (i.e., expanded in the longitudinal direction) of an area of the packaged absorbent product 50 that is folded along the upper folding line 61 in the drawing. In FIG. 8, this folding line 61 is indicated by the thin line. FIGS. 5 and 6 described above are views that are obtained by releasing the folded absorbent product 1*b* to show a developed state of the area folded along the two folding lines 61. In FIGS. 5 and 6, the two folding lines 61 are indicated by thin lines. In the example shown in FIG. 5, the two folding lines 61 are located in the longitudinal central region 102.

In the example shown in FIG. 6, each of the two folding lines 61 is a straight line approximately parallel to the width direction. One of the folding lines 61 is provided at a position displaced on one side in the longitudinal direction from the center in the longitudinal direction of the absorbent product 1*b*, and the other folding lines 61 is provided at a position displaced on the other side in the longitudinal direction from this center of the absorbent product 1*b*. In the packaged absorbent product 50 before use, an area 63 that is folded along the upper folding line 61 in FIG. 7 and an area 64 that is folded along the lower folding line 61 are secured to each other with an adhesive tape 65, with the area 63 being superimposed on the area 64. Side edge portions of the packaging sheet 51 are sealed by, for example, thermal compression bonding on both sides in the width direction of the packaged absorbent product 50.

In use of the packaged absorbent product 50, the adhesive tape 65 is peeled off to develop the folding along the two folding lines 61. At this time, the sealing of the packaging sheet 51 on both side edges of the packaged absorbent product 50 is also removed. Then, the packaging sheet 51 is peeled off and removed from the absorbent product 1*b*, and the absorbent product 1*b* is secured to the exterior product with the adhesive portion 27*b* provided on the back sheet 23.

The adhesive portion 27*b* shown in FIG. 5 is approximately the same as the adhesive portion 27 shown in FIG. 3, except that the adhesive elements 271*b* are arranged on the back sheet 23 to avoid the folding lines 61. Specifically, the shape and arrangement of the central adhesive elements 272*b* in the longitudinal central region 102 are approximately the same as those of the central adhesive elements 272 shown in FIG. 3, except that two central adhesive elements that are located on the two folding lines 61 are omitted. The shape and arrangement of the end adhesive elements 273*b* in each longitudinal end region 103 are approximately the same as those of the end adhesive elements 273 shown in FIG. 3.

In the example shown in FIG. 5, a shortest distance D7 in the longitudinal direction between two central adhesive elements 272*b* that are adjacent to each other in the longitudinal direction while sandwiching one folding line 61 therebetween, among the central adhesive elements 272*b*, is greater than a shortest distance D8 in the longitudinal direction between each pair of central adhesive elements 272*b* that are adjacent to each other in the longitudinal direction with no folding line 61 sandwiched therebetween. Thus, the interval in the longitudinal direction of the central adhesive elements 272*b* (i.e., an average interval) is greater than the distance D8 and shorter than the distance D7. For example, the distance D8 may be the same as the aforementioned interval P1.

A shortest distance D9 (hereinafter, also referred to as an "alienation distance D9") in the longitudinal direction between one folding line 61 and one central adhesive element 272*b* that is closest to this folding line 61 in the longitudinal direction, among the central adhesive elements 272*b*, is in the range of 5 mm to 50 mm. If the alienation distance D9 between the central adhesive element 272*b* and the folding line 61 is set to be greater than or equal to 5 mm, it is possible to reduce the occurrence of twisting of the central adhesive element 272*b* caused by the influences of the folding line 61 in cases such as where the packaged absorbent product 50 is folded during the manufacturing process. If the alienation distance D9 is set to be less than or equal to 50 mm, it is possible to reduce the possibility that the strength to secure the absorbent product 1*b* to the exterior product may become insufficient in the vicinity of the folding line 61.

In cases such as where the packaged absorbent product 50 is folded during the manufacturing process, the back sheet 23 may become deformed largely within a relatively wide range in the vicinity of the folding lines 61, and this may result in the formation of creases or the like on the back sheet 23. Therefore, it is preferable to set the alienation distance D9 between the central adhesive elements 272*b* and the folding line 61 to a relatively large value in order to reduce the occurrence of twisting of the central adhesive element 272*b* caused by the influences of the folding line 61. Specifically, for example, the alienation distance D9 may be set to a value greater than the alienation distance D1 between the central adhesive element 272*b* and one longitudinal-side boundary portion 203.

In the above-described example, the folding lines 61 are located in the longitudinal central region 102, and the central adhesive elements 272*b* are arranged to avoid the folding lines 61, but the present invention is not limited thereto. For example, at least one of the folding lines 61 may be located in either of the longitudinal end regions 103, and the end adhesive elements 273*b* in this longitudinal end region 103 may be arranged to avoid the folding line 61.

As described above, the absorbent product 1*b* before use is folded along the folding line 61 extending in the width direction, and the adhesive elements 271*b* are arranged on the back sheet 23 to avoid the folding line 61. Accordingly, it is possible to reduce the occurrence of twisting of the adhesive elements 271*b* caused by the influences of the folding line 61 in cases such as where the packaged absorbent product 50 is folded during the manufacturing process.

It is also preferable that the shortest distance D9 in the longitudinal direction between one folding line 61 and one adhesive element 271*b* that is located on the first area 201 in the adhesive portion 27*b* (i.e., the aforementioned first adhesive element, and in the above-described example, the central adhesive element 272*b*) is greater than the shortest distance D1 in the longitudinal direction between each of the pair of longitudinal-side boundary portions 203 and the first adhesive element (in the above-described example, the central adhesive element 272*b*). This further reduces the occurrence of twisting of the adhesive elements 271*b* caused by the influences of the folding line 61.

The absorbent products 1, 1*a*, and 1*b* described above may be modified in various ways.

For example, the alienation distances D1 to D3 in the absorbent product 1 are not limited to the ranges described above, and may be modified in various ways. The alienation distances D4 to D6 in the absorbent product 1*a* are not limited to the ranges described above, and may be modified in various ways. Similarly, the distances D7 and D8 and the alienation distance D9 in the absorbent product 1*b* are not limited to the ranges described above, and may be modified in various ways.

In the longitudinal central region 102 of the absorbent product 1, the central adhesive elements 272 may also be provided outside the pair of lateral-side boundary portions 204 in the width direction (i.e., outside the first area 201 of the absorber 20 in the width direction) in approximately the same manner as on the first area 201. The same applies to the absorbent products 1*a* to 1*b*.

Figure 9:
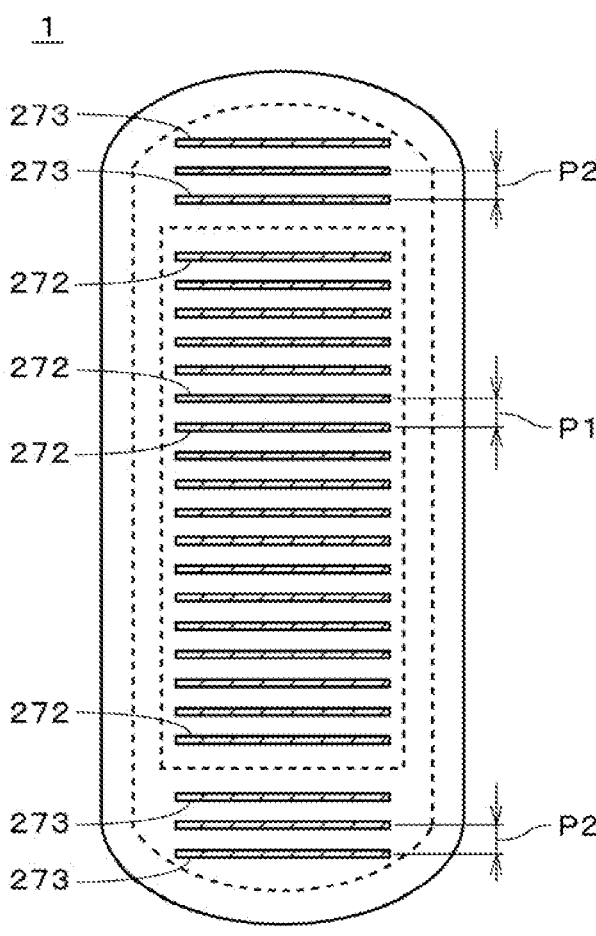
FIG. 9 is a bottom view of another absorbent product.
Figure 10:
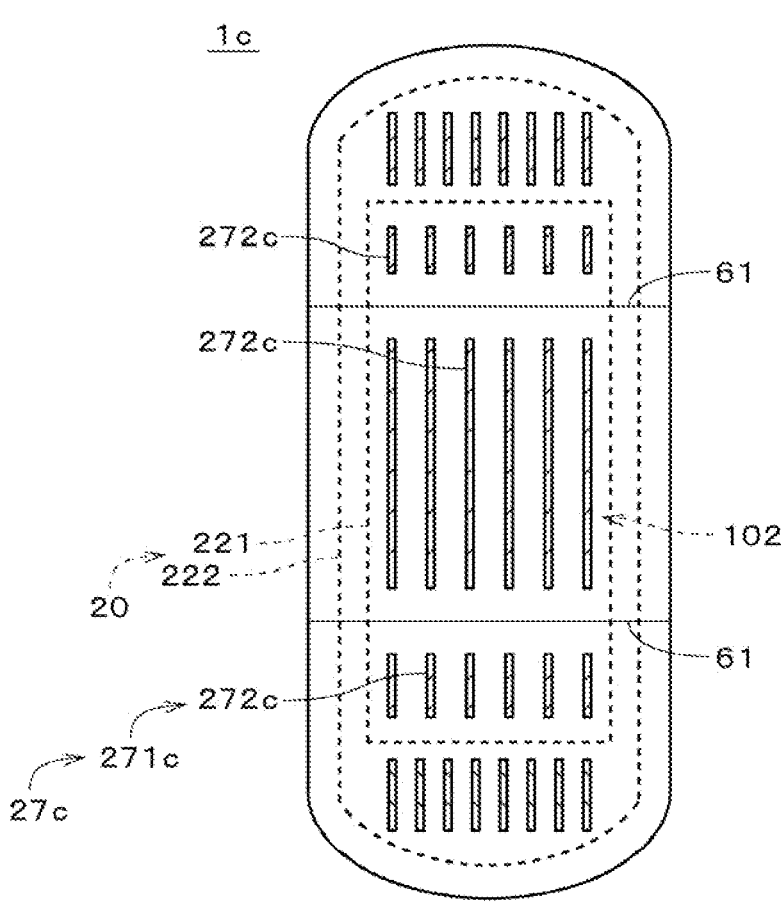
FIG. 10 is a bottom view of another absorbent product.

In the absorbent product 1, the interval P1 of the central adhesive elements 272 may be shorter than the interval P2 of the end adhesive elements 273. Alternatively, as shown in FIG. 9, the interval P1 of the central adhesive elements 272 may be approximately the same as the interval P2 of the end adhesive elements 273. Similarly in the absorbent product 1*a*, the interval P3 of the central adhesive elements 272 may be shorter than or approximately the same as the interval P4 of the end adhesive elements 273.

In the absorbent product 1*b* shown in FIG. 5, the adhesive elements 271*b* each extend in the width direction and are aligned in the width direction to avoid the folding lines 61, but the present invention is not limited thereto. For example, as in the absorbent product 1*c* shown in FIG. 10, the adhesive elements 271*c* of the adhesive portion 27*c* may each extend in the longitudinal direction and may be aligned in the width direction to avoid the folding lines 61. In the example shown in FIG. 10, in the longitudinal central region 102, the central adhesive elements 272*c* extending in approximately parallel with the longitudinal direction are divided in the longitudinal direction in the vicinity of the two folding lines 61. In this way, if the adhesive elements 271*c* are arranged on the back sheet 23 to avoid the folding lines 61, it is possible to reduce the occurrence of twisting of the adhesive elements 271*c* caused by the influences of the folding lines 61 in approximately the same manner as in the absorbent product 1*b* shown in FIG. 5.

In the absorbent products 1*b* and 1*c*, the number of folding lines 61 may be one, or may be three or more. The absorbent products 1*b* and 1*c* may omit the packaging sheet 51 and may be folded solely along the folding lines 61 and placed in a package or the like.

In the absorbent product 1, the central adhesive elements 272 may overlap the lateral-side boundary portion 204 in plan view. The same applies to the absorbent products 1*a* to 1*c*. In the absorbent product 1*b*, the central adhesive elements 272*b* may overlap the folding line 61 in plan view. The same applies to the absorbent product 1*c*.

In the absorbent product 1, the above-described first adhesive elements arranged on the first area 201 and the above-described second adhesive elements arranged on the second area 202 may extend in different directions. The same applies to the absorbent products 1*a* to 1*c*.

The shapes of the absorbent products 1 and 1*a* to 1*c*, the first absorbent sheet 221, and the second absorbent sheet 222 in plan view are not limited to the examples described above, and may be modified in various ways. For example, the absorbent products 1 and 1*a* to 1*c*, the second absorbent sheet 222, and the first absorbent sheet 221 may have approximately oblong shapes that are greater in length than width. Alternatively, the absorbent product 1 and the second absorbent sheet 222 in plan view may have an hourglass shape whose central portion in the longitudinal direction becomes constricted (i.e., has a smaller width).

The absorber 20 does not necessarily have to have a laminated structure of the first absorbent sheet 221, which is an SAP sheet, and the second absorbent sheet 222, which is a liquid absorptive board. The structure of the absorber 20 may be modified in various ways. For example, the first absorbent sheet 221 may be a sheet or the like formed of pulverized pulp fibers (so-called cotton pulp) or a mixture of the aforementioned high absorbent material and cotton pulp, or may be liquid-absorptive paper or hydrophilic nonwoven fabric. For example, the second absorbent sheet 222 may be an SAP sheet, cotton pulp, or a mixture of the aforementioned high absorbent material and cotton pulp.

The absorber 20 may have a structure in which absorbent sheets are laminated in three or more layers. The absorber 20 does not necessarily have to include a plurality of absorbent sheets and, for example, may be an integral member that is formed of cotton pulp and in which the cotton pulp in the first area 201 has a greater thickness than the cotton pulp in the second area 202.

Both of the crosswise end portions of the absorbent product 1 may be provided with a pair of side sheets. Each side sheet includes a side-sheet securing portion that is secured onto the top sheet 21 with an adhesive or the like and a side-sheet standing portion that stands up from the side-sheet securing portion toward the wearer side. This favorably prevents leakage of urine or the like from the sides of the absorbent product 1 (i.e., side leakage). The same applies to the absorbent products 1*a* to 1*c*.

The above-described structure of the absorbent product 1 may be applied to auxiliary absorbent tools other than absorbent pads for light urinary incontinence, and may also be applied to various absorbent products (e.g., disposal diapers) other than the auxiliary absorbent tools.

The configurations of the above-described preferred embodiment and variations may be appropriately combined as long as there are no mutual inconsistencies.

While the invention has been shown and described in detail, the foregoing description is in all aspects illustrative and not restrictive. It is therefore understood that numerous modifications and variations can be devised without departing from the scope of the invention.

REFERENCE SIGNS LIST 1, 1*a* to 1*c* absorbent product
20 absorber
21 top sheet
23 back sheet
27, 27*a* to 27*c* adhesive portion
61 folding line
201 first area
202 second area
203 longitudinal-side boundary portion
204 lateral-side boundary portion
22 first absorbent sheet
222 second absorbent sheet
223 first upper sheet
224 high absorbent material
225 first lower sheet
271, 271*a* to 271*c* adhesive element

The invention claimed is:

1. An absorbent product for receiving body waste from a wearer, the absorbent product comprising:
   a top sheet that is liquid-permeable;
   a back sheet that is liquid-repellent or liquid-impermeable;
   an absorber arranged between the top sheet and the back sheet; and
   an adhesive portion arranged on a surface of the back sheet on an opposite side to a wearer side,
   wherein:
   the absorber includes a first area located in a central portion in a longitudinal direction;
   the absorber includes a second area that is thinner than the first area and contiguous to the first area on both sides in the longitudinal direction of the first area;
   the absorber includes longitudinal-side boundary portions between the first area and the second area on both sides in the longitudinal direction of the first area;
   each of the longitudinal-side boundary portions extends in a width direction;
   the adhesive portion includes first adhesive elements and second adhesive elements arranged on the back sheet to avoid the longitudinal-side boundary portions;
   each of the first adhesive elements extends in one of a longitudinal direction in the first area or a width direction in the first area, and the first adhesive elements are aligned in the other of the longitudinal direction in the first area or the width direction in the first area;
   each of the second adhesive elements extends in one of a longitudinal direction in the second area or a width direction in the second area, and the second adhesive elements are aligned in the other of the longitudinal direction in the second area or the width direction in the second area;
   the second area is contiguous to the first area on both sides in the width direction of the first area;
   the absorber includes lateral-side boundary portions between the first area and the second area on both sides in the width direction of the first area;
   each of the lateral-side boundary portions extends in the longitudinal direction;
   the first adhesive elements and the second adhesive elements are arranged on the back sheet to avoid the lateral-side boundary portions; and
   a shortest distance in the width direction between each of the lateral-side boundary portions and the first adhesive elements is greater than or equal to 1 mm and less than or equal to 7.5 mm.

2. The absorbent product according to claim 1, wherein:
   the absorber includes a first absorbent sheet configured to secure a particulate or fibrous high absorbent material to a main surface of a sheet support member with an adhesive;
   the absorber includes a second absorbent sheet that is longer than the first absorbent sheet in the longitudinal direction and arranged between the first absorbent sheet and either of the back sheet or the top sheet;
   the first area of the absorber is an area where the first absorbent sheet and the second absorbent sheet overlap each other in a thickness direction; and
   the second area of the absorber is an area of the second absorbent sheet that extends outward from the first absorbent sheet.

3. The absorbent product according to claim 1, wherein:
   an interval of adhesive elements that are located between the longitudinal-side boundary portions, among the first adhesive elements and the second adhesive elements, are greater than an interval of adhesive elements that are located outward of the longitudinal-side boundary portions in the longitudinal direction, among the first adhesive elements and the second adhesive elements.

4. The absorbent product according to claim 1, wherein;
the absorbent product is configured to be folded along a folding line that extends in the width direction; and
the first adhesive elements and the second adhesive elements are arranged on the back sheet to avoid the folding line.

5. The absorbent product according to claim 4, wherein:
a shortest distance in the longitudinal direction between the folding line and the first adhesive elements is greater than a shortest distance in the longitudinal direction between each of the longitudinal-side boundary portions and the first adhesive elements.

* * * * *